(12) United States Patent
McAlister et al.

(10) Patent No.: US 6,986,748 B2
(45) Date of Patent: Jan. 17, 2006

(54) MULTIPLE BIOPSY APPARATUS AND RELATED METHOD OF USE

(75) Inventors: Gary McAlister, Franklin, MA (US); Paul Sanders, Raleigh, NC (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/411,146

(22) Filed: Apr. 11, 2003

(65) Prior Publication Data

US 2004/0034310 A1 Feb. 19, 2004

Related U.S. Application Data

(63) Continuation of application No. 10/218,915, filed on Aug. 15, 2002, now abandoned.

(51) Int. Cl.
*A61B 10/00* (2006.01)

(52) U.S. Cl. .................. 600/564; 600/565; 606/167

(58) Field of Classification Search ............... 600/562, 600/564–567; 604/19, 22, 27, 28, 35; 606/159–161, 606/167, 170, 171, 1
See application file for complete search history.

(56) References Cited

U.S. PATENT DOCUMENTS

| | | | |
|---|---|---|---|
| 5,106,364 A | 4/1992 | Hayafuji et al. | |
| 5,425,376 A | 6/1995 | Banys et al. | |
| 5,458,112 A | 10/1995 | Weaver | |
| 5,601,585 A | 2/1997 | Banik et al. | |
| 5,779,648 A | 7/1998 | Banik et al. | |
| 5,980,469 A | * 11/1999 | Burbank et al. | 600/567 |
| 6,241,687 B1 | * 6/2001 | Voegele et al. | 600/566 |
| 6,485,436 B1 | * 11/2002 | Truckai et al. | 600/564 |
| 2003/0191413 A1 | * 10/2003 | Damarati | 600/567 |
| 2003/0229292 A1 | * 12/2003 | Hibner et al. | 600/566 |

FOREIGN PATENT DOCUMENTS

| | | |
|---|---|---|
| WO | 00/44285 | 8/2000 |
| WO | WO 02/062230 A1 | 8/2002 |

OTHER PUBLICATIONS

International Search Report (ISR) for International Application No. PCT/US03/22205, mailed on Nov. 26, 2003.

* cited by examiner

*Primary Examiner*—Charles Marmor
(74) *Attorney, Agent, or Firm*—Finnegan Henderson Farabow Garrett & Dunner, L.L.P.

(57) ABSTRACT

An endoluminal biopsy device is provided with a proximal actuation mechanism attached to a distal sampler by at least one elongate member. The distal sampler includes a distal inner portion defining a plurality of chambers, each configured to receive a tissue sample, and a distal outer portion defining a cutting mechanism opening having a cutting edge adjacent the cutting mechanism opening. The distal outer portion is configured so that, when the cutting mechanism opening aligns with one of the plurality of chambers, the distal outer portion covers the remaining chambers. A related method for the use of such an endoluminal biopsy device also is provided.

48 Claims, 5 Drawing Sheets

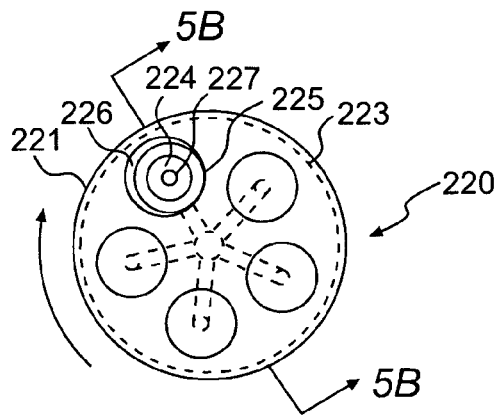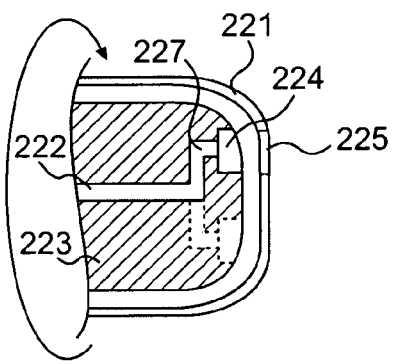
FIG. 5A   FIG. 5B
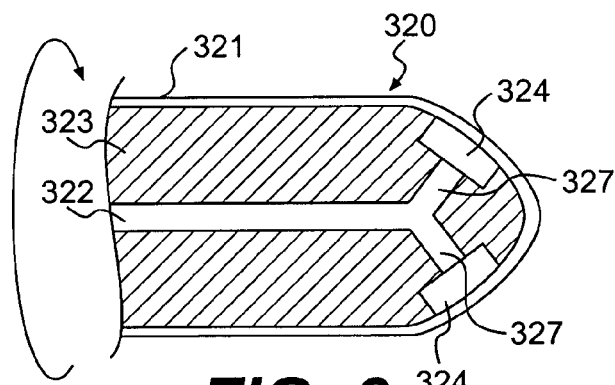
FIG. 6
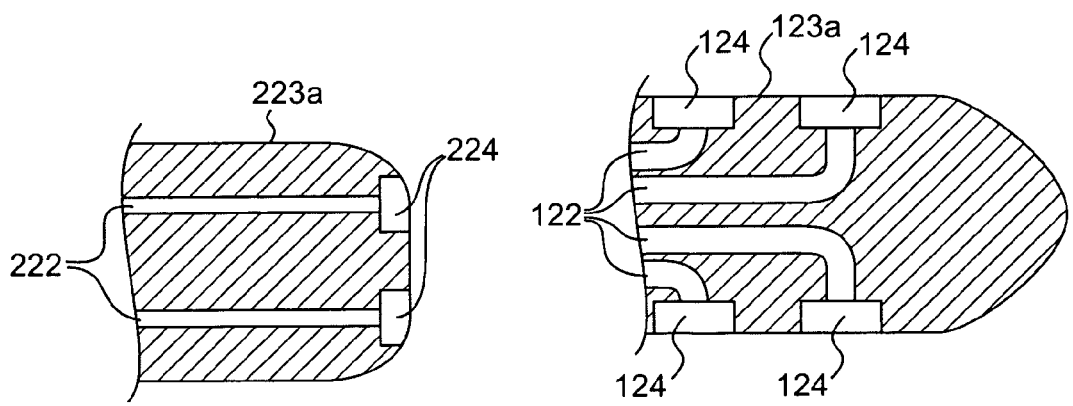
FIG. 7   FIG. 8

MULTIPLE BIOPSY APPARATUS AND RELATED METHOD OF USE

This is a continuation of application Ser. No. 10/218,915, filed Aug. 15, 2002, now abandoned.

BACKGROUND OF THE INVENTION

1. Field of the Invention

The present invention relates to a biopsy device for use in endoluminal procedures. More particularly, the present invention relates to a biopsy device that is capable of taking multiple biopsies.

2. Description of the Related Art

An endoluminal procedure is a medical procedure that takes place in one of the many tubes, or lumens, within the human body. These endoluminal procedures may take place in vascular, gastrointestinal, or air exchange lumens and may involve disease diagnosis and/or treatment. Millions of endoluminal procedures are performed each year in hospitals around the world.

Endoluminal procedures are often performed utilizing a device known as an endoscope. An endoscope is a tube, either rigid or flexible, that is introduced through a lumen (opening) in the human body, such as the mouth or rectum. The endoscope may simply be used to hold open the lumen for examination, but it may also carry light(s), visioning system(s), or other tools to be used in the procedure. An open or "working" channel is usually present within the endoscope into which the endoscopist can insert and withdraw a myriad of endoluminal diagnostic or treatment devices.

In some endoscopic procedures, biopsies (tissue samples) are obtained. Tissue samples can be examined in a laboratory to determine the presence of a pathological disorder, such as a malignancy. Often the sample may need to be obtained from deep within the body cavity medical sampling instruments. It is usually best to sample at various locations where the disorder is suspected so that the presence and progress of the disease (if any) may be determined. The samples may need to be catalogued according to the location from which each sample is taken, and the integrity of the samples should be maintained for subsequent lab analysis.

Existing endoluminal devices are capable of taking multiple biopsies without removing the device, but there are disadvantages to the devices currently in use. Usually the device must be moved each time a biopsy is taken so that the location of the biopsy is not completely accurate. In addition, current biopsy devices often store the tissue samples in one long cylindrical chamber. These samples may not be separated in any way and contamination between samples often occurs.

In addition to these disadvantages, current biopsy devices often utilize a mechanical means to pull away and cut the sample. This may create a variation in the amount of tissue taken each time, and this can also cause either more tissue than necessary to be taken or possibly not enough tissue to perform the desired analysis.

SUMMARY OF THE INVENTION

The advantages and purposes of the invention will be set forth in part in the description which follows, and in part will be obvious from the description, or may be learned by practice of the invention. These advantages and purposes will be realized and attained by way of the elements and combinations particularly pointed out in the appended claims.

To attain the advantages and in accordance with the purpose of the invention, as embodied and broadly described herein, one aspect of the invention is directed to an endoluminal device for taking tissue samples. The endoluminal device for taking a plurality of tissue samples includes a proximal actuation mechanism attached to a distal sampler by at least one elongate member. The distal sampler includes a distal inner portion defining a plurality of chambers, each configured to receive a tissue sample, and a distal outer portion defining a cutting mechanism opening having a cutting edge adjacent the cutting mechanism opening. The distal outer portion is configured so that, when the cutting mechanism opening aligns with one of the plurality of chambers, the distal outer portion covers the remaining chambers.

According to another aspect, the distal sampler includes a chamber opening corresponding to each of the plurality of chambers through which the corresponding chamber can receive the tissue sample.

According to yet another aspect, the distal inner portion defines a vacuum inlet corresponding to each of the plurality of chambers, each vacuum inlet configured to permit a vacuum to be applied to the corresponding chamber.

In another aspect, each vacuum inlet is in fluid communication with a vacuum channel that is capable of communicating with a vacuum source.

In yet another aspect, each vacuum inlet is in fluid communication with a separate vacuum channel to provide the vacuum to the corresponding chamber.

According to another aspect, the proximal actuation mechanism includes a mechanism for alternately applying the vacuum source to each of the separate corresponding vacuum channels.

In another aspect, the cutting mechanism opening has a substantially similar shape as each chamber opening.

According to yet another aspect, the cutting edge is configured to sever the tissue sample as the distal outer portion moves to align with one of the remaining chambers.

In yet another aspect, the distal inner portion is configured to keep a tissue sample obtained within one of the plurality of chambers separate from tissue samples obtained within the remainder of the plurality of chambers.

According to another aspect, each of the chambers has approximately the same volume.

According to another aspect, one of the plurality of chambers has a volume different from another of the plurality of chambers.

In another aspect, the distal inner portion and the distal outer portion are substantially cylindrical and substantially coaxial.

In yet another aspect, the distal outer portion is rotatably movable relative to the distal inner portion.

According to another aspect, the plurality of sample chambers are located on a distal face of the distal inner portion and positioned radially about a central axis of the distal inner portion and the cutting mechanism opening is located on a distal end of the distal outer portion.

According to yet another aspect, the distal outer portion is substantially closed at a distal end of the distal sampler and substantially covers the distal face of the distal inner portion.

According to another aspect, the distal face of the distal inner portion is substantially perpendicular to a longitudinal axis of the distal inner portion.

In another aspect, the distal outer portion is axially movable relative to the distal inner portion.

In yet another aspect, the plurality of sample chambers are located about a periphery of the distal inner portion and the cutting mechanism opening is located about a periphery of the distal outer portion.

According to another aspect, the cutting edge is integral to the distal outer portion.

In a further aspect, the distal outer portion comprises a substantially rigid material.

In yet another aspect, the distal outer portion is material comprised of a rigid plastic or surgical stainless steel.

According to another aspect, the at least one elongate member comprises a first conduit and a second conduit and the proximal actuation mechanism comprises a proximal outer portion connected to the distal outer portion by the first conduit and a proximal inner portion connected to the distal inner portion by a second conduit.

In another aspect, the proximal outer portion includes one or more finger rings and the proximal inner portion includes a thumb ring.

In yet another aspect, the proximal outer portion includes a first actuator knob and the proximal inner portion includes a second actuator knob.

According to another aspect, the invention is directed to a method of obtaining a plurality of tissue samples. The method includes inserting into a body lumen a biopsy device with a distal sampler defining first and second biopsy chambers, positioning the distal sampler proximate tissue to be sampled, aligning a cutting mechanism opening with the first biopsy chamber to expose the first biopsy chamber to the tissue to be sampled while the second biopsy chamber is covered, receiving a first tissue sample into the first biopsy chamber, and severing the first tissue sample.

According to yet another aspect, the method also includes aligning the cutting mechanism opening with the second biopsy chamber to expose the second biopsy chamber to tissue to be sampled while the first biopsy chamber is covered, receiving a second tissue sample into the second biopsy chamber, and severing the second tissue sample.

In another aspect, the distal sampler remains in substantially the same position relative to the body lumen when each of the first and second tissue samples is severed.

In yet another aspect, the severing of the first and second tissue samples is performed by moving a single cutting mechanism relative to the first and second biopsy chambers respectively.

According to another aspect, the receiving of the first and second tissue samples into the first and second biopsy chambers respectively includes applying a vacuum to the first and second biopsy chambers respectively.

According to yet another aspect, the applying a vacuum to the first and second biopsy chambers includes applying the vacuum through first and second vacuum inlets that correspond to the first and second biopsy chambers respectively.

In a further aspect, the biopsy device remains in the body lumen between the severing of the first tissue sample and the severing of the second tissue sample.

In yet a further aspect, the vacuum source is applied selectively to the first and second biopsy chambers by actuation of a vacuum line selection mechanism located at a proximal end of the biopsy device.

In another aspect, the aligning comprises actuating a proximal actuation mechanism of the biopsy device to translate movement of the proximal actuation mechanism to a distal sampler of the biopsy device.

In yet another aspect, actuating the proximal actuation mechanism comprises moving a proximal outer portion relative to a proximal inner portion to cause rotational and axial movement of a distal outer portion with respect to a distal inner portion, and the distal outer portion defines a cutting mechanism for severing the tissue and the distal inner portion defines the first and second biopsy chambers.

The foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 5A is an end view of a distal sampler according to an alternative exemplary embodiment;

FIG. 5B is a partial section view of the distal sampler of FIG. 5A taken along section line 5B—5B;

FIG. 6 is a partial section view of another alternative embodiment of a distal sampler according to the invention;

FIG. 7 is a partial section view of an alternative embodiment of an internal part of a distal sampler having separate vacuum lines for each sample chamber;

FIG. 8 is a partial section view of an alternative embodiment of an internal part of a distal sampler having separate vacuum lines for each sample chamber;

DESCRIPTION OF THE PREFERRED EMBODIMENTS

Reference will now be made in detail to the present preferred and exemplary embodiments of the invention, examples of which are illustrated in the accompanying drawings. Wherever possible, the same reference numbers will be used throughout the drawings to refer to the same or like parts.

Figure 1:
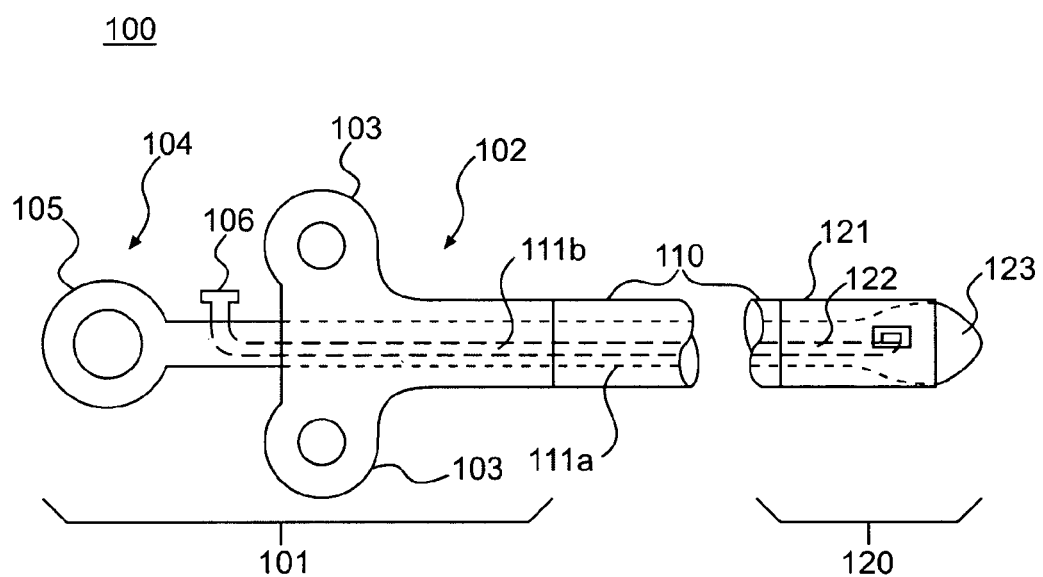
FIG. 1 is a plan view of a biopsy sampling device according to an embodiment of the present invention, showing a proximal actuation mechanism and a distal sampler.

FIG. 1 depicts a sampling device 100 according to an embodiment of the present invention. Sampling device 100 includes a proximal actuation mechanism 101 and a distal sampler 120. Actuation mechanism 101 includes a finger ring assembly 102 that includes finger rings 103. Instead of finger ring assembly 102, it could also be possible to utilize a spool-like arrangement or any other suitable mechanism known in the art. Finger ring assembly 102 attaches to a flexible elongate member, or connecting conduit 110. Connecting conduit 110 may be, for example, a braided tube made of nylon, polyethylene, or other suitable material known to one of skill in the art. Conduit 110 fixedly attaches at its distal end to an outer portion (or sleeve) 121 of distal sampler 120.

Actuation mechanism 101 further includes a thumb ring assembly 104 that includes thumb ring 105 and extends within finger ring assembly 102. Thumb ring assembly 104 translates longitudinally and rotates relative to finger ring assembly 102. Thumb ring assembly 104 is integral with an elongate conduit 111a defining a vacuum lumen 111b. Conduit 111a may be made of polyethylene or another suitable material to provide a suction tube of sufficient strength so as not to collapse on itself when suction is applied. Vacuum lumen 111b could also comprise a separate tube, also of sufficient strength so as not to collapse on itself when suction is applied, extending within conduit 111b. Vacuum lumen 111b runs from a vacuum port 106 through conduit 111a and ultimately connects with a vacuum channel 122 located within an inner portion 123 of distal sampler 120. Vacuum port 106 is provided to allow for the sampling device to be connected to a vacuum source (not depicted).

Conduit 111a ultimately connects with inner portion 123 of distal sampler 120. In one exemplary embodiment, conduit 111a may be integral with portion 123, i.e. a unitary part. In the configuration shown, relative movement of finger ring assembly 102 and thumb ring assembly 104, is translated via conduits 110 and 111a to outer portion (or sleeve) 121 and inner portion 123, respectively. Thus, as thumb ring 105 rotates with respect to finger rings 103, that rotational motion will cause inner portion 123 to rotate with respect to outer potion (or sleeve) 121. Axial motion may also translate from proximal actuation mechanism 101 to distal sampler 120 in a similar manner. As will be described below, this rotational and axial motion may be used to take biopsy samples with device 100.

Figure 2:
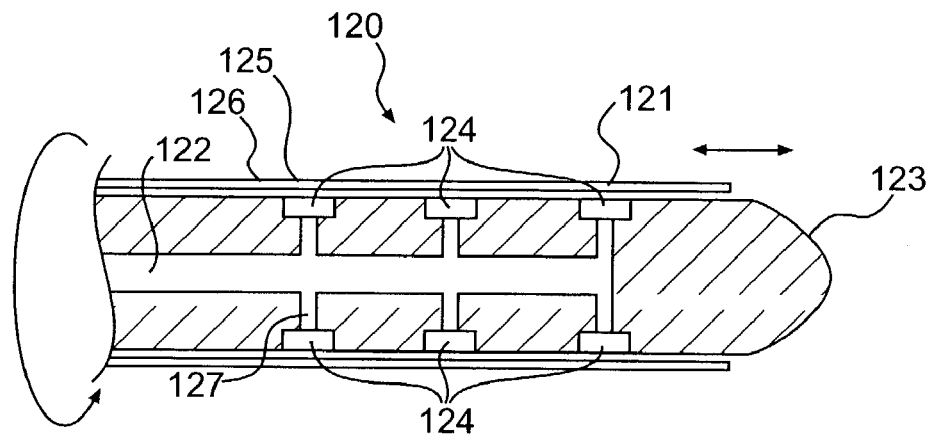
FIG. 2 is a partial section view of the distal sampler of the biopsy sampling device shown in FIG. 1.

FIG. 2 shows a cut-away portion of distal sampler 120. As can be seen, the vacuum channel 122 extends through a portion of inner portion 123 and branches off to a plurality of sample chambers 124 via vacuum inlet ports 127. Preferably, each vacuum inlet port 127 is of a sufficiently small size so that a tissue sample obtained within a chamber does not exit the chamber via the vacuum inlet port 127. Vacuum channel 122, as well as inlet ports 127, may be defined by a flexible or rigid tubing material suitable for a vacuum line located within distal sampler 120, or vacuum channel 122 and inlet ports 127 could be manufactured as a part of distal sampler 120, such as by molding or machining.

Outer portion 121 includes a cutting mechanism opening 125 that includes a cutting mechanism 126 located along at least one edge of opening 125. Outer portion 121 may be made of surgical stainless steel, a rigid plastic or any other material suitable for medical devices. Cutting mechanism 126 may be a sharpened cutting edge of opening 125, for example, if portion 121 were made of stainless steel or any other material capable of having an edge honed to a cutting sharpness. Cutting mechanism 126 alternatively may be a pre-manufactured cutting edge that is affixed to an edge of opening 125, for example by mechanical fastening, welding, brazing or any other suitable manner for affixing.

As is depicted by the arrows in FIG. 2, outer portion 121 is capable of moving both axially and rotatably with respect to inner portion 123. To allow for portion 121 to slide more easily along inner portion 123, a coating, such as a lubricant like hydrogel, could be used between portion 121 and inner portion 123. In addition, in order to maintain a seal between portion 121 and inner portion 123, especially in the vicinity of chambers 124, sealing means such as O-rings or other suitable sealing devices may be provided surrounding each of chambers 124. Portion 121 and inner portion 123 also may be manufactured with tight tolerances to maintain proper sealing, thus eliminating the need for additional sealing devices.

Biopsy sampling device 100 having distal sampler 120 may be used in connection with an endoscope or other similar device. In operation, distal sampler 120 of biopsy sampling device 100 is inserted in a lumen of the endoscope that has been inserted in a patient, until distal sampler 120 reaches an area of tissue to be sampled. Distal sampler 120 may then be positioned so that one or more of chambers 124 are proximate the area of tissue to be sampled. The user may then actuate thumb ring 105 with respect to finger rings 103 so as to position cutting mechanism opening 125 of outer portion 121 over one of the plurality of sample chambers 124. Once cutting mechanism opening 125 is positioned over one of sample chambers 124, suction may be applied in the selected chamber to cause tissue to enter the chamber. Portion 121 may then be moved in an axial sliding motion relative to inner portion 123, again by actuating thumb ring 105 with respect to finger rings 103, so that cutting mechanism 126 cuts the tissue from the patient. As portion 121 moves to cut the tissue, it seals the chamber so that only the sample taken at that time is located in the chamber.

The user then may actuate portion 121 into a position so that opening 125 is positioned over a different chamber, by rotation, axial movement, or both, so that a subsequent tissue sample may be captured in a similar fashion as just described. This procedure may be repeated until all chambers have a tissue sample or until all necessary samples have been obtained. As illustrated by the Figures, each retrieved sample may be isolated within its chamber so as to reduce the possibility of contamination between that sample and any other samples.

While the device is shown utilizing suction to draw the tissue sample into the chamber, alternatives could be used to accomplish this task. For example, in the case of a hanging polyp or tumor, or any similarly protruding segment of tissue, the distal sampler could be positioned so that a chamber engulfs the tissue without the use of suction. With the tissue then inside the chamber, portion 121 could be moved to cut the tissue. A further alternative may include a mechanical grabbing device at the base of the chamber. The mechanical grabbing device may have a jaw assembly or other mechanism that may be actuated at the proximal end of the biopsy sampling device by the user. This grabbing device may grasp and pull the tissue to be sampled into the chamber so that the tissue may then be cut by the movement of the portion 121. The mechanical grabbing assembly may also be spear-like and/or have barbs or hooks for grasping tissue and holding onto the tissue as tissue is pulled into the chamber.

The biopsy sampling device may also include indicators, such as color-coding or other such identification means, on portions of the proximal operator end 101. For example, axial and radial tick marks could be placed on portions of thumb ring assembly 104 and/or finger ring assembly 102 to denote relative positions of assemblies 102, 104 that correspond to each of the plurality of chambers 124 located within distal sampler 120. Each indicator can correspond to color-coding or other identification means associated with each chamber at distal sampler 120. This identification could allow the operator to relate the specific chamber in use to that indicated at the proximal end when remotely viewing distal sampler 120 during the procedure. For example, the user in this way may determine that he or she is viewing and working with the proximal-most chamber, as determined from the matching identification between the operator handle and the chamber.

Figure 3:
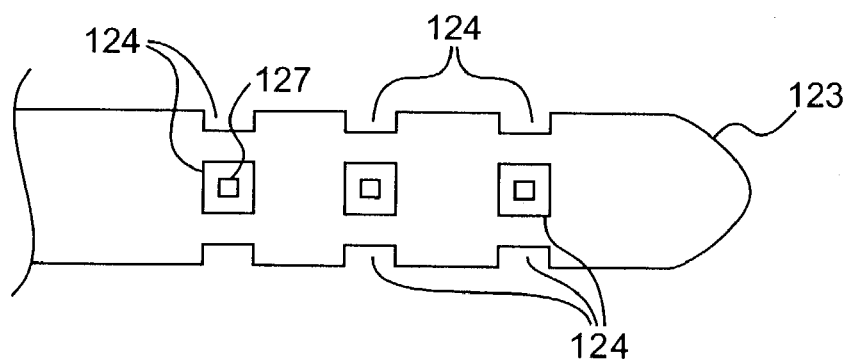
FIGS. 3 and 4 are partial plan views of two exemplary embodiments of an internal portion of the distal sampler shown in FIG. 2.
Figure 4:
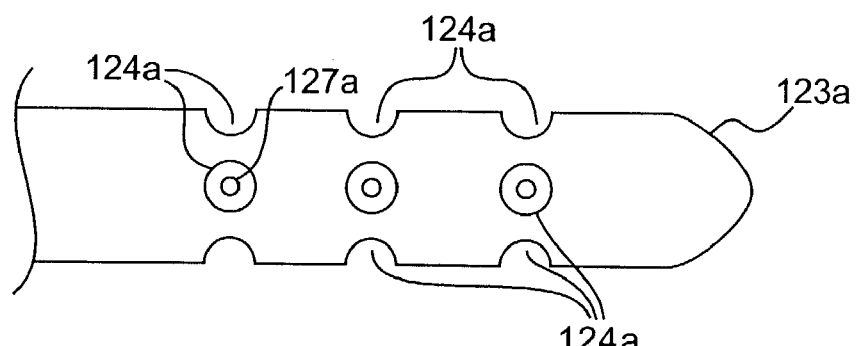

FIG. 3 is a partial view of inner portion 123 of FIG. 2. Chambers 124 and vacuum inlet ports 127 are both depicted as having a generally square shape. FIG. 4 shows an alternative embodiment of an interior portion 123a. Interior portion 123a has circular shaped chambers 124a and vacuum inlet ports 127a. Although the vacuum inlet ports and sample chambers of interior portions 123, 123a are depicted as having the same shape, a vacuum inlet port could have a different shape from its corresponding sample chamber. Also, although square and circular shaped chambers and inlet ports are depicted, one of ordinary skill in the art would understand that substantially any shape could be utilized for the sample chambers and inlet ports.

In addition, each of the chambers in the distal inner portion may be the same size and/or volume or different sizes and/or volumes to allow for different size samples to be taken. By using a vacuum to suck the tissue sample into a chamber that is of a known volume, a more precise volume of tissue may be taken each time. Having sample chambers of different volumes within the same distal sampler may allow the operator more flexibility during a given procedure by being able to take samples of various sizes without having to remove the device from the patient.

FIGS. 3 and 4 depict distal inner portions 123, 123a as having sample chambers 124, 124a in four axial rows of three chambers equally spaced around a periphery of inner portions 123, 123a. Other chamber configurations are possible, such as more or fewer axial rows spaced equally or unequally around the periphery as well as rows containing more or fewer than three chambers each. It could also be possible to have axial rows containing chambers of different size within the row or each row could contain chambers of the same size within the row, but different from the size of chambers in another row or other rows. In addition, it could be possible to have the chambers arranged on the periphery of the distal inner portion in a helical pattern or any other desired pattern. Other chamber configurations could also be possible.

Figure 12:
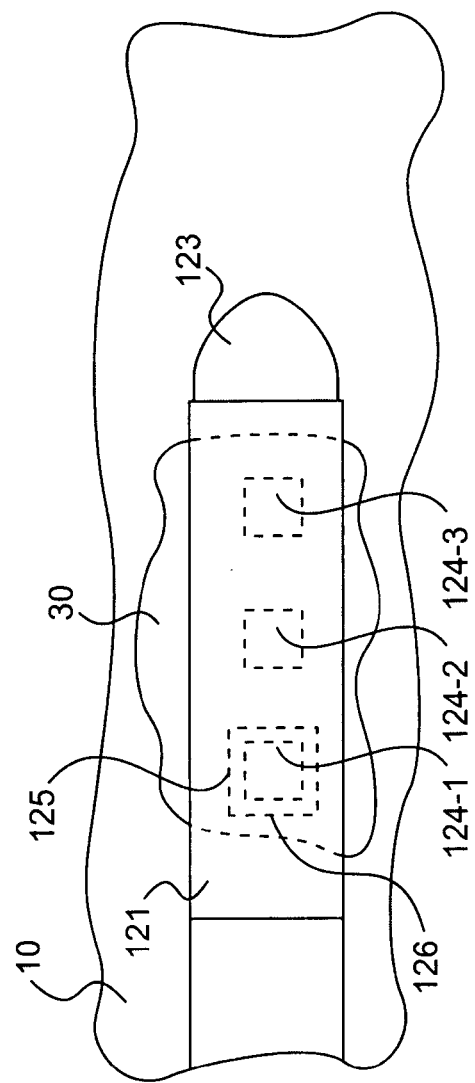
FIG. 12 is a plan view of the distal sampler of the biopsy sampling device shown in FIG. 1 in a body lumen.

As shown in FIG. 12, a distal end of a device similar to that depicted in FIG. 1 is positioned over a tumor 30 in a body lumen 10 such as an intestine. A first chamber 124-1 may be exposed to the tumor 30 to be sampled so that the tissue sample can be received into chamber 124-1. Portion 121 may then be moved so that the cutting mechanism (or cutting edge) 126 may sever the tissue sample. An additional advantage of this type of configuration is that with adjacent chambers 124-1, 124-2, and 124-3 being a predetermined distance apart, if inner portion 123 is maintained in the same position while taking samples along the tumor 30 from the various chambers, the size of the tumor may be discerned. In use, the device can be placed with an open chamber just at the beginning of or just before the location of the tumor. Then each successive chamber can be used in the manner described above to remove tissue samples along the length of the tumor concluding in a final sample that contains only healthy tissue. In this manner, by counting the number of chambers that contain tissue from the tumor, the approximate size of the tumor can be determined.

FIGS. 5A and 5B show an alternative embodiment of a distal sampler 220. According to this embodiment, rather than being located along the perimeter of distal sampler 220, chambers 224 are located at a distal face that is substantially perpendicular to a longitudinal axis of sampler 220. Chambers 224 are arranged in a radial configuration about the longitudinal axis of the device. An outer portion 221, rather than being open-ended as in the previous embodiment, encloses and covers the end of sampler 220. A device of this type could be suitable for procedures in larger lumens where there is more room for maneuverability, such as the stomach, where it may be possible to position the distal face of the device proximate the area to be sampled. This configuration may also be desirable for use in other locations, such as portions of a lumen with a sharp turn where it may be difficult to navigate such that positioning the distal face of the device proximate the area to be sampled is easier than positioning along the side of the device. This configuration also may be used in combination with a device having a deflectable distal end, so that the distal face of the distal sampler may be turned towards tissue to be sampled.

The configuration shown in FIGS. 5A and 5B differs from the previous embodiment in that only rotational motion is necessary to access various of chambers 224. In operation, portion 221 could be rotated such that opening 225 communicates with one of chambers 224, allowing suction to be applied to vacuum channel 222, port 227, chamber 224, and ultimately to an area of tissue to be sampled. The application of suction may draw the tissue into chamber 224. Portion 221 then could be rotated again so as to allow a cutting mechanism (or cutting edge) 226 to sever the tissue and opening 225 to move in position over the next chamber. Distal sampler 220 could be repositioned to align the next chamber with another area to be sampled, or, if the next chamber is already in a desired location for another sample, distal sampler 220 could remain in the same position for the next sample to be taken.

FIG. 6 depicts a further embodiment of a device 320 similar to that of FIGS. 5A and 5B. In this embodiment, however, chambers are not located on a distal face that is substantially perpendicular to the longitudinal axis of the device, as in FIG. 5B. Instead, chambers 324 are located on a rounded, or angled, face of distal sampler 320. Portion 321 is configured to substantially match the shape of inner portion 323, and is configured to be rotatable about inner portion 323. As with distal sampler 220, distal sampler 320 has a vacuum channel 322 that branches into vacuum inlets 327 that communicate with each of the sample chambers 324.

FIGS. 7 and 8 depict alternative embodiments of inner portions whereby, instead of having a single vacuum channel in communication with each chamber via a vacuum inlet, each chamber 124, 224 is in communication with its own vacuum channel 122, 222. Vacuum channels 122, 222 may, in turn, lead to a vacuum channel selection device 315 at the proximal end of the device, as seen in FIGS. 9 and 10.

Figure 9:
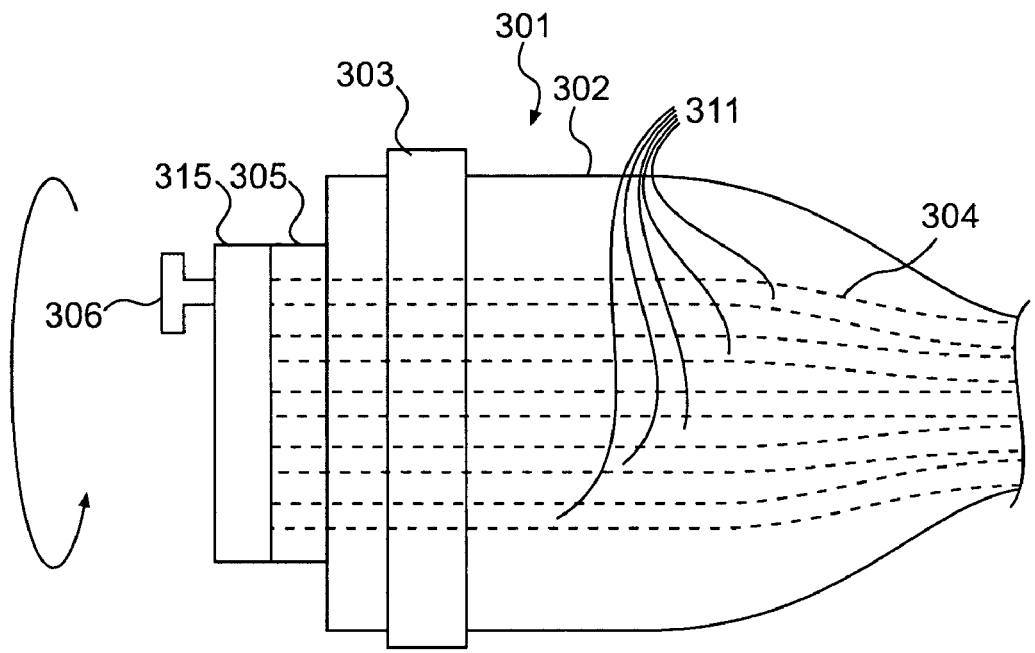
FIG. 9 is a partial plan view of a proximal actuation mechanism according to an alternative embodiment of the present invention having a vacuum selection device.
Figure 10:
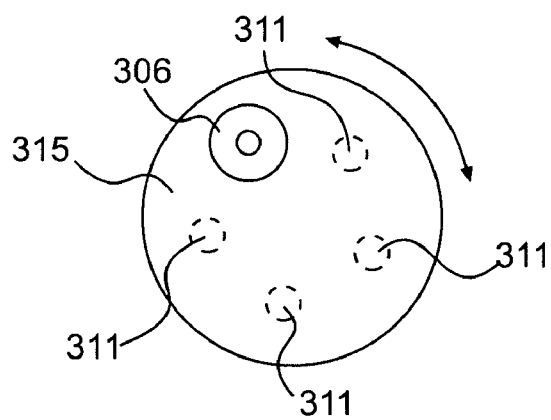
FIG. 10 is an end view of the vacuum line selection device of FIG. 9.

FIGS. 9 and 10 show plan and end views, respectively, of an alternative embodiment of a proximal actuator 301 having a vacuum selection device 315, especially suited for the embodiments shown in FIGS. 7 and 8. In this embodiment, a plurality of vacuum lines 311 is located within an inner portion 304. Each vacuum line 311 corresponds to one of the vacuum channels 122, 222 in the embodiment shown in FIGS. 7 and 8. Vacuum lines 311 alternatively could be integral with vacuum channels 122, 222, for example in the form of a tube running from vacuum selection device 315 to chambers 124, 224. Vacuum lines 311 could also comprise tubing that is a separate from, and connects to, vacuum channels 122, 222. In another configuration, a portion of each of vacuum lines 311 could be formed or machined into inner portion 304 with a remainder of each of lines 311 comprising tubing that connects from proximal inner portion 304 to distal inner portion 123a, 223a.

Proximal actuator 301 also has two actuator rings or knobs 303 and 305. Knobs 303, 305 are affixed to outer portion 302 and inner portion 304, respectively. Outer and inner portions 302, 304 are, in turn, integral with and/or fixedly connected to outer and inner conduits that extend to the distal end of the device, much like conduits 110 and 111a in FIG. 1. Proximal actuator 301 operates in a generally similar fashion as the thumb/finger ring configuration of actuator 101 insofar as movement of proximal outer portion 302 relative to proximal inner portion 304 which translates to conduits 110 and 111a and to distal outer portion 121 and distal inner portion 123. With this configuration, an operator may grasp actuator knobs 303, 305 and create both axial and rotational movement of outer portion 302 relative to inner portion 304.

Vacuum selection device 315 is capable of rotational movement with respect to knob 305 so that vacuum port 306 may align and communicate separately with each of vacuum lines 311. In this manner, an operator may apply suction to each chamber independent of the other chambers. This configuration also allows for substantially complete isolation between the various chambers.

In order to facilitate the rotation of vacuum selection device 315 with respect to knob 305, proximal actuator 301 could include a feature to reversibly lock vacuum selection device 315 in place on knob 305. In order to achieve this rotation without affecting the positioning of distal end 120, vacuum selection device 315 could rotate to detent positions whereby an operator would have to grip both knob 305 and vacuum selection device 315 to select the various lines. Vacuum selection device 315 could also include a locking means that unlocks to allow for free rotation of vacuum selection device 315 with respect to knob 305 until a desired vacuum line is selected. The locking means could then lock vacuum selection device 315 in place over a selected vacuum line with respect to knob 305.

Figure 11:
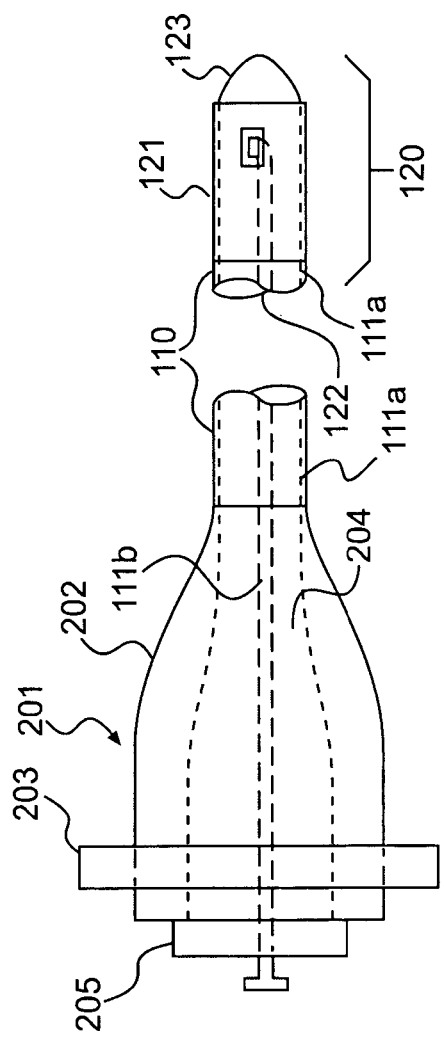
FIG. 11 is a plan view of a biopsy sampling device showing a proximal actuation mechanism according to an alternative embodiment of the present invention.

FIG. 11 shows another embodiment of a biopsy sampling device. This embodiment includes a distal sampler 120 like that shown and described in connection with FIG. 1. In this embodiment, however, distal sampler 120 is attached to a proximal actuator 201 that is in some respects like actuator 301 shown and described in connection with FIG. 9. Proximal actuator 201, however, communicates with a single vacuum channel 111b, so a vacuum selection device is not needed. Proximal actuator 201 includes a first actuator knob 203 connected to outer portion 202, which in turn is connected to outer portion 121 of distal sampler 120 via flexible conduit 110. A second actuator knob 205 connects to inner portion 204 that houses vacuum line 111b and eventually connects via conduit 111a to the distal inner portion 123 of distal sampler 120. Knobs 203, 205 act as handles similar to knobs 303, 305 of actuator 301. An operator may grip knobs 203, 205 and create both rotational and axial movement of inner portion 204 with respect to outer portion 202. This movement may then be translated to the distal end 120 for operation of portion 121 with respect to inner portion 123 for biopsy purposes as described above.

Other configurations for inner portion and outer portion may be used depending on the desired application. For example, the cutting mechanism opening may be used to take samples without using a cutting edge. In this procedure, the device could act as a head that would selectively open chambers to allow tissue to be sucked in. The sucking motion alone could be sufficient to pull the tissue sample away from the patient. Once the tissue sample is completely contained within the chamber, the distal outer portion would move, this time without cutting any tissue, to isolate the sample in the selected chamber and proceed to the next chamber.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoluminal device for taking a plurality of tissue samples, comprising:
   a proximal actuation mechanism attached to a distal sampler by an elongate member,
   wherein the distal sampler includes:
      a distal inner portion having a longitudinal axis and defining a plurality of chambers, each configured to receive a tissue sample; and
      a distal outer portion defining a cutting mechanism opening and a cutting edge adjacent the cutting mechanism opening, the distal outer portion being axially and rotatably movable relative to the distal inner portion,
   wherein the cutting mechanism opening faces a direction transverse to the longitudinal axis of the distal inner portion,
   wherein the distal outer portion is configured so that, when the cutting mechanism opening aligns with one of the plurality of chambers, the distal outer portion covers at least one of the remaining chambers, and
   wherein actuation of the proximal actuation mechanism causes the distal outer portion to move axially and rotatably relative to the distal inner portion.

2. The endoluminal device of claim 1, further comprising a chamber opening corresponding to each of the plurality of chambers through which the corresponding chamber can receive the tissue sample.

3. The endoluminal device of claim 2, wherein the cutting mechanism opening has a substantially similar shape as each chamber opening.

4. The endoluminal device of claim 1, wherein the distal inner portion defines a vacuum inlet corresponding to each of the plurality of chambers, each vacuum inlet configured to permit a vacuum to be applied to the corresponding chamber.

5. The endoluminal device of claim 4, wherein each vacuum inlet is in fluid communication with a vacuum channel that is capable of communicating with a vacuum source.

6. The endoluminal device of claim 5, wherein the vacuum channel includes a plurality of discrete vacuum channels, each corresponding to and in fluid communication with the respective vacuum inlet.

7. The endoluminal device of claim 6, wherein the proximal actuation mechanism includes a mechanism for alternately applying the vacuum source to each of the discrete vacuum channels.

8. The endoluminal device of claim 1, wherein the cutting edge is configured to sever the tissue sample as cutting mechanism opening moves out of alignment with the one of the plurality of chambers.

9. The endoluminal device of claim 1, wherein the distal inner portion is configured to keep a tissue sample obtained within one of the plurality of chambers separate from tissue samples obtained within the remainder of the plurality of chambers.

10. The endoluminal device of claim 1, wherein each of the chambers has approximately the same volume.

11. The endoluminal device of claim 1, wherein one of the plurality of chambers has a volume different from another of the plurality of chambers.

12. The endoluminal device of claim 1, wherein the distal inner portion and the distal outer portion are substantially cylindrical and substantially coaxial.

13. The endoluminal device of claim 1, wherein the chambers are positioned radially about the longitudinal axis of the distal inner portion.

14. The endoluminal device of claim 1, wherein the plurality of sample chambers are located about a periphery of the distal inner portion and the cutting mechanism opening is located about a periphery of the distal outer portion.

15. The endoluminal device of claim 1, wherein the cutting edge is integral to the distal outer portion.

16. The endoluminal device of claim 1, wherein the distal outer portion comprises a substantially rigid material.

17. The endoluminal device of claim 1, wherein the elongate member comprises a first conduit and a second conduit, and
wherein the proximal actuation mechanism comprises a proximal outer portion connected to the distal outer portion by the first conduit and a proximal inner portion connected to the distal inner portion by the second conduit.

18. The endoluminal device of claim 17, wherein the proximal outer portion includes one or more finger rings and the proximal inner portion includes a thumb ring.

19. The endoluminal device of claim 17, wherein the proximal outer portion includes a first actuator knob and the proximal inner portion includes a second actuator knob.

20. A method of obtaining a plurality of tissue samples, comprising:
inserting into a body lumen a biopsy device with a distal sampler having a longitudinal axis and defining first and second biopsy chambers;
positioning the distal sampler proximate tissue to be sampled;
aligning a cutting mechanism opening that faces a direction transverse to the longitudinal axis of the distal sampler with the first biopsy chamber to expose the first biopsy chamber to the tissue to be sampled while the second biopsy chamber is covered, the cutting mechanism opening being axially and rotatably movable relative to the first and second biopsy chambers;
receiving a first tissue sample into the first biopsy chamber; and
actuating a proximal actuation mechanism to move the cutting mechanism opening at least one of axially and rotatably relative to the first biopsy chamber, thereby severing the first tissue sample.

21. The method of claim 20, further comprising aligning the cutting mechanism opening with the second biopsy chamber to expose the second biopsy chamber to tissue to be sampled while the first biopsy chamber is covered;
receiving a second tissue sample into the second biopsy chamber; and
severing the second tissue sample.

22. The method of claim 21, wherein the distal sampler remains in substantially the same position relative to the body lumen when each of the first and second tissue samples are severed.

23. The method of claim 21, wherein the severing of the second tissue sample is performed by moving the cutting mechanism opening relative to the second biopsy chamber.

24. The method of claim 21, wherein the receiving of the first and second tissue samples into the first and second biopsy chambers respectively includes applying a vacuum to the first and second biopsy chambers respectively.

25. The method of claim 24, wherein the applying a vacuum to the first and second biopsy chambers includes applying the vacuum through first and second vacuum inlets that correspond to the first and second biopsy chambers respectively.

26. The method of claim 24, wherein the vacuum is applied selectively to the first and second biopsy chambers by actuation of a vacuum line selection mechanism located at a proximal end of the biopsy device.

27. The method of claim 21, wherein the biopsy device remains in the body lumen between the severing of the first tissue sample and the severing of the second tissue sample.

28. The method of claim 20, wherein the aligning comprises actuating the proximal actuation mechanism of the biopsy device to translate movement of the proximal actuation mechanism to a distal sampler of the biopsy device.

29. The method of claim 20, wherein actuating the proximal actuation mechanism comprises moving a proximal outer portion relative to a proximal inner portion to cause rotational and axial movement of a distal outer portion with respect to a distal inner portion,
wherein the distal outer portion defines the cutting mechanism opening for severing tissue and the distal inner portion defines the first and second biopsy chambers.

30. An endoluminal device for taking a plurality of tissue samples, comprising:
a proximal actuation mechanism attached to a distal sampler by an elongate member,
wherein the distal sampler includes:
a distal inner portion defining a plurality of chambers, each configured to receive a tissue sample; and
a distal outer portion defining a cutting mechanism opening and a cutting edge adjacent the cutting mechanism opening,
wherein the distal outer portion is axially and rotatably movable over and relative to the distal inner portion,
wherein the distal outer portion is configured so that, when the cutting mechanism opening aligns with one of the plurality of chambers, the distal outer portion covers at least one of the remaining chambers, and
wherein actuation of the proximal actuation mechanism causes the distal outer portion to move axially and rotatably relative to the distal inner portion.

31. The endoluminal device of claim 30, wherein at least two of the plurality of chambers are located along a longitudinal axis of the distal inner portion.

32. The endoluminal device of claim 30, wherein the distal inner portion defines a vacuum inlet corresponding to each of the plurality of chambers, each vacuum inlet configured to permit a vacuum to be applied to the corresponding chamber.

33. The endoluminal device of claim 32, wherein each vacuum inlet is in fluid communication with a vacuum channel that is capable of communicating with a vacuum source.

34. The endoluminal device of claim 30, wherein the distal inner portion and the distal outer portion are substantially cylindrical and substantially coaxial.

35. The endoluminal device of claim 30, wherein at least one of the plurality of chambers is located on a distal face of the distal inner portion.

36. The endoluminal device of claim 30, wherein the chambers are positioned radially about a longitudinal axis of the distal inner portion.

37. The endoluminal device of claim 30, wherein the plurality of chambers are located about a periphery of the distal inner portion and the cutting mechanism opening is located about a periphery of the distal outer portion.

38. The endoluminal device of claim 30, wherein the cutting edge is integral to the distal outer portion.

39. The endoluminal device of claim 30, wherein the elongate member comprises a first conduit and a second conduit, and
wherein the proximal actuation mechanism comprises a proximal outer portion connected to the distal outer portion by the first conduit and a proximal inner portion connected to the distal inner portion by the second conduit.

40. A method of obtaining a plurality of tissue samples, comprising:
inserting into a body lumen a biopsy device with a distal sampler having a longitudinal axis and defining first and second biopsy chambers;
positioning the distal sampler proximate tissue to be sampled;
aligning a cutting mechanism opening with the first biopsy chamber to expose the first biopsy chamber to the tissue to be sampled while the second biopsy chamber is covered, the cutting mechanism opening being axially and rotatably movable relative to the first and second biopsy chambers;
receiving a first tissue sample into the first biopsy chamber; and
actuating a proximal actuation mechanism to cause the cutting mechanism opening to move axially and rotatably relative to the first biopsy chamber, thereby severing the first tissue sample.

41. The method of claim 40, further comprising aligning the cutting mechanism opening with the second biopsy chamber to expose the second biopsy chamber to tissue to be sampled while the first biopsy chamber is covered;
receiving a second tissue sample into the second biopsy chamber; and
severing the second tissue sample.

42. The method of claim 40, wherein the distal sampler remains in substantially the same position relative to the body lumen when each of the first and second tissue samples are severed.

43. The method of claim 40, wherein receiving the first tissue sample into the first biopsy chamber comprises applying a vacuum to the first biopsy chamber.

44. An endoluminal device for taking a plurality of tissue samples, comprising:
a proximal actuation mechanism attached to a distal sampler by an elongate member,
wherein the distal sampler includes:
a distal inner portion defining a plurality of chambers, each configured to receive a tissue sample; and
a distal outer portion defining a cutting mechanism opening and a cutting edge adjacent the cutting mechanism opening,
wherein the distal outer portion is configured so that, when the cutting mechanism opening aligns with one of the plurality of chambers, the distal outer portion covers the remaining chambers,
wherein the distal inner portion defines a vacuum inlet corresponding to each of the plurality of chambers, each vacuum inlet configured to permit a vacuum to be applied to the corresponding chamber,
wherein each vacuum inlet is in fluid communication with a vacuum channel that is capable of communicating with a vacuum source, and
wherein the vacuum channel includes a plurality of discrete vacuum channels, each corresponding to and in fluid communication with the respective vacuum inlet.

45. The endoluminal device of claim 44, wherein the proximal actuation mechanism includes a mechanism for alternately applying the vacuum source to each of the discrete vacuum channels.

46. An endoluminal device for taking a plurality of tissue samples, comprising:
a proximal actuation mechanism attached to a distal sampler by an elongate member, the elongate member comprising a first conduit and a second conduit,
wherein the distal sampler includes:
a distal inner portion defining a plurality of chambers, each configured to receive a tissue sample; and
a distal outer portion defining a cutting mechanism opening and a cutting edge adjacent the cutting mechanism opening,
wherein the distal outer portion is configured so that, when the cutting mechanism opening aligns with one of the plurality of chambers, the distal outer portion covers the remaining chambers,
wherein the proximal actuation mechanism comprises a proximal outer portion connected to the distal outer portion by the first conduit and a proximal inner portion connected to the distal inner portion by the second conduit, and
wherein the proximal outer portion includes one or more finger rings and the proximal inner portion includes a thumb ring.

47. An endoluminal device for taking a plurality of tissue samples, comprising:
a proximal actuation mechanism attached to a distal sampler by an elongate member, the elongate member comprising a first conduit and a second conduit,
wherein the distal sampler includes:
a distal inner portion defining a plurality of chambers, each configured to receive a tissue sample; and
a distal outer portion defining a cutting mechanism opening and a cutting edge adjacent the cutting mechanism opening,
wherein the distal outer portion is configured so that, when the cutting mechanism opening aligns with one of the plurality of chambers, the distal outer portion covers the remaining chambers,
wherein the proximal actuation mechanism comprises a proximal outer portion connected to the distal outer portion by the first conduit and a proximal inner portion connected to the distal inner portion by the second conduit, and
wherein the proximal outer portion includes a first actuator knob and the proximal inner portion includes a second actuator knob.

48. A method of obtaining a plurality of tissue samples, comprising:
inserting into a body lumen a biopsy device with a distal sampler defining first and second biopsy chambers;
positioning the distal sampler proximate tissue to be sampled;

aligning a cutting mechanism opening of the biopsy device with the first biopsy chamber to expose the first biopsy chamber to the tissue to be sampled while the second biopsy chamber is covered;

receiving a first tissue sample into the first biopsy chamber; and severing the first tissue sample, wherein the aligning comprises actuating a proximal actuation mechanism of the biopsy device to translate movement of the proximal actuation mechanism to the distal sampler of the biopsy device, and wherein actuating the proximal actuation mechanism comprises moving a proximal outer portion relative to a proximal inner portion to cause rotational and axial movement of a distal outer portion with respect to a distal inner portion, wherein the distal outer portion defines the cutting mechanism opening for severing tissue and the distal inner portion defines the first and second biopsy chambers.

* * * * *

UNITED STATES PATENT AND TRADEMARK OFFICE
CERTIFICATE OF CORRECTION

PATENT NO. : 6,986,748 B2  
DATED : January 17, 2006  
INVENTOR(S) : Gary McAlister et al.

It is certified that error appears in the above-identified patent and that said Letters Patent is hereby corrected as shown below:

Column 10,
Line 60, "as cutting" should read -- as the cutting --.

Column 11,
Line 45, "culling" should read -- cutting --.

Signed and Sealed this

Twenty-first Day of March, 2006

JON W. DUDAS
*Director of the United States Patent and Trademark Office*